United States Patent [19]

Silvestrini

[11] Patent Number: 4,554,288

[45] Date of Patent: Nov. 19, 1985

[54] USE OF BENDAZAC AND ITS SALTS IN THE TREATMENT OF RETINITIS PIGMENTOSA

[75] Inventor: Bruno Silvestrini, Rome, Italy

[73] Assignee: Aziende Chimiche Riunite Angelini Francesco A.C.R.A.F. S.p.A., Rome, Italy

[21] Appl. No.: 597,504

[22] Filed: Apr. 6, 1984

[30] Foreign Application Priority Data

Apr. 18, 1983 [IT]  Italy ................ 20649 A/83

[51] Int. Cl.$^4$ ............................................. A61K 31/40
[52] U.S. Cl. ..................................... 514/418; 514/912
[58] Field of Search ............... 424/273 N; 514/418, 514/912

[56] References Cited

U.S. PATENT DOCUMENTS

| | | | |
|---|---|---|---|
| Re. 27,253 | 12/1971 | Palazzo | 424/273 N |
| 3,625,970 | 12/1971 | Ambrus | 424/273 N |
| 4,282,237 | 8/1981 | Silvestrini | 424/273 N |
| 4,352,813 | 10/1982 | Silvestrini et al. | 424/273 N |
| 4,451,477 | 5/1984 | Silvestrini et al. | 424/273 N |

OTHER PUBLICATIONS

The Lancet; Apr. 10, 1982, pp. 849–850–Testa et al.
Chem. Abst., 70:66559(r)(1969)–Silvestrini et al.
Chem. Abst., 99:152,048(d)(1983)–Silvestrini et al.

*Primary Examiner*—Douglas W. Robinsion
*Attorney, Agent, or Firm*—Ladas & Parry

[57] ABSTRACT

It was discovered that bendazac, or (1-phenylmethyl-1H-indazol -3-yl)oxy acetic acid, when administered in a form suitable to obtain therapeutic tissue concentrations, determine an improvement in *retinitis pigmentosa*. The lysine salt of bendazac is well adapted for this use owing to its good oral absorption.

10 Claims, No Drawings

USE OF BENDAZAC AND ITS SALTS IN THE TREATMENT OF RETINITIS PIGMENTOSA

*Retinitis pigmentosa* is a retinal degeneration characterized by the following manifestations: night blindness, progressive loss of peripheral vision, eventually leading to total blindness; ophthalmoscopic changes consist in dark mosaic-like retinal pigmentaion, attenuation of the retinal vessels, waxy pallor of the optic disc, and in the advanced forms, macular degeneration. In some cases there can be a lack of pigmentation (Pearlman et al., 1976). *Retinitis pigmentosa* can be associated to degenerative opacity of the vitreous body, and cataract. A number of more complex syndromes are often associated to this disease, such as Usher's syndrome, responsible for deafness; Laurence-Moon syndrome, characterized by hypogonadism, mental retardation and obesity; Refsum's syndrome which can lead to mental retardation and dwarfism. Family history is prominent in *retinitis pigmentosa;* the pattern of inheritance may be autosomal recessive, autosomal dominant, or X-linked; the autosomal recessive form is the most common and can occur sporadically (McKusick, 1978). Disease incidence varies from 1/2000 to 1/7000 according to the type of investigation and geographic location (Ammann et al., 1965; Merin and Auerbach, 1976).

*Retinitis pigmentosa* was first described a century ago; its pathogenesis is, nevertheless, still unknown despite the variety of hypotheses postulated as to its origin (Wirth, 1982). Not only is there no effective and safe treatment available for this disease at present, but the rational planning of pharmacological investigations is also very difficult; the lack of basic knowledge is, in fact, accompanied by the lack of animal models which suitably reproduce the corresponding human pathology, thereby enabling the laboratory study of potentially active substances. This explains why the problem of treating *retinitis pigmentosa* is generally based on working hypotheses confirmed by indirect experimental evidence. A typical example is the working hypothesis, prompted by the discovery of a local dopamine deficiency, which led to the study in man of a dopaminergic drug with encouraging results (Wirth, 1982).

The discovery claimed in this patent is connected to the working hypothesis that *retinitis pigmentosa* is the result of a defect in the physiological mechanisms of protection against the photo-oxidative processes involving free radicals; consequently, the free radicals which continuously form on the retina seem to cause, with a photo-oxidative process, progressive damage to the structure. According to this hypothesis abnormal pigment deposition within the retina and the increased threshold in the perception of light stimuli is, initially, nothing more than a secondary defensive process: biologically, these mechanisms seem just as important as the skin pigmentation following exposure to sun rdiations. Retinal degeneration is the result of a deficiency in the protective physiological mechanisms and the secondary defensive processes mentioned above. On the basis of this interpretation, the search for drugs active on *retinitis pigmentosa* has two distinct objectives:

(a) normalize the physiological mechanisms of protection against the photo-oxidative processes involving free radicals. Unfortunately, this research approach is practically impossible due to the lack of necessary basic knowledge.

(b) attenuate the biological effects of sun radiations on the retina.

Previous investigations conducted in these laboratories demonstrated that bendazac prevents protein denaturation produced by U.V. rays (Silvestrini et al., 1969); in view of the above considerations, it appeared potentially interesting in the treatment of *retinitis pigmentosa* as a drug capable of attenuating the biological effects of sun radiations on the retina. This possibility was confirmed by the recent observation that bendazac also has a protective effect on photo-oxidative processes linked to free radicals in the photohemolysis test according to the method by Finazzi-Agrò et al. (1979). This test is based on the fact that protoporphyrin has, on some biological materials, a photosensitizing effect seemingly linked to the formation of free radicals (Lamola et al., 1973; De Goeij et al., 1975; Girotti, 1976; Strom et al., 1977). In the above test bendazac showed a protective dose-related effect starting at concentrations around 3 $\mu$g/ml. Bendazac, as a lysine salt, is already used for the oral treatment of cataract (Italian Patent Application N. 49790A/81 filed on Nov. 26, 1981; U.S. patent application Ser. No. 386,468 filed on June 8, 1982).

On the basis of theoretical considerations and the above mentioned experimental data, a clinical study was performed with bendazac lysine salt in *retinitis pigmentosa*. The patient population consisted of ten subjects with diagnostically confirmed advanced *retinitis pigmentosa*. The patients were submitted to ophthalmological examination prior to the beginning of the study and then given bendazac lysine salt at the dose of 500 mg three times daily for a period of 6 months. Ophthalmological tests were repeated at the following times: 1, 2, 4 and 6 months. Table I summarizes these data. Typical changes of the fundus included vessel restricting, chorio-retinal dystrophy with pigmentation and optic nerve atrophy. In the ERG (electroretinogram), a typical change involved in *retinitis pigmentosa* was a curve with a decrease in the scotopic component and monophasic wave of the cone function without photochromatic intervals. A check up 1 month after the beginning of treatment showed an improvement in dark adaptation curve and ERG. Another 3 patients reported improvement in visual acuity and dark adaptation, which however, were not confirmed by the tests performed. Two months after the beginning of treatment, 5 patients showed an improvement in the dark adaptation curve, ERG and visual acuity; 3 of these patients also reported a significant increase in visual field. Four and 6 months later the results were unchanged. No severe drug-related side effects were observed necessitating the discontinuation of treatment.

Although the results of this study were obtained by administering bendazac orally in the form of lysine salt, available data on this drug indicate that it is capable of affecting *retinitis pigmentosa* in other salt forms, pharmaceutical forms, or eye-drops. In this connection please refer to the patents mentioned above.

TABLE 1

Results obtained with bendazac lysine salt in retinitis pigmentosa

| Case No. | Sex | Age | Characteristics of fundus | Visual field R | Visual field L | Dark adaptation curve | E.R.G. |
|---|---|---|---|---|---|---|---|
| 1 | M | 65 | typical changes | | tubular 15° | characteristic | flat |
| 2 | M | 28 | " | | tubular 5° | " | " |
| 3 | M | 30 | " | | tubular 15° | " | " |
| 4 | M | 50 | " | | tubular 5° | " | " |
| 5 | M | 40 | " | not detectable | | " | " |
| 6 | M | 50 | " | 5° | tubular 10° | " | " |
| 7 | F | 52 | " | | tubular 5° | " | " |
| 8 | F | 38 | " | | tubular 10° | " | " |
| 9 | F | 32 | " | | tubular 5° | " | " |
| 10 | F | 61 | " | not detectable | | " | " |

I claim:

1. A method for the treatment of *retinitis pigmentosa* in a human which comprises administering to said human a therapeutically effective amount of bendazac.

2. A method according to claim 1, wherein the bendazac is administered orally.

3. A method according to claim 2, wherein bendazac is administered in daily doses of about 600–900 mg to produce blood levels in the range of 20–40 γ/ml.

4. A method according to claim 3, wherein bendazac is in the form of its dihydrate lysine salt.

5. A method according to claim 4, wherein the bendazac lysine salt is administered at doses of about 1000–1500 mg/daily.

6. A method according to claim 5, wherein said bendazac lysine salt, is administered in two or more daily doses.

7. A method for the treatment of *retinitis pigmentosa* according to claim 1, in which bendazac is applied directly to the eye.

8. A method according to claim 7, in which the bendazac is in a pharmaceutical vehical at concentrations of about 0.1–1%.

9. A method according to claim 8, in which the bendazac is in the form of its dihydrate lysine salt.

10. A method according to claim 9, in which the bendazac is administered two or three times daily.

* * * * *